United States Patent
Mahna (10) Patent No.: US 11,826,342 B1
(45) Date of Patent: Nov. 28, 2023

(54) CANNABIDIOL FORMULATION FOR ALLEVIATING PAIN AND A METHOD OF MANUFACTURING

(71) Applicant: Saaransh Mahna, Great Falls, VA (US)

(72) Inventor: Saaransh Mahna, Great Falls, VA (US)

(73) Assignee: Saaransh Mahna, Great Falls, VA (US)

( * ) Notice: Subject to any disclaimer, the term of this patent is extended or adjusted under 35 U.S.C. 154(b) by 0 days.

(21) Appl. No.: 17/953,844

(22) Filed: Sep. 27, 2022

(51) Int. Cl.
| | | |
|---|---|---|
| A61K 31/335 | (2006.01) | |
| A61K 31/201 | (2006.01) | |
| A61K 31/616 | (2006.01) | |
| A61K 31/352 | (2006.01) | |
| A61K 45/06 | (2006.01) | |
| A61K 31/05 | (2006.01) | |

(52) U.S. Cl.
CPC ............ *A61K 31/352* (2013.01); *A61K 31/05* (2013.01); *A61K 45/06* (2013.01)

(58) Field of Classification Search
USPC ........................................ 514/165, 456, 560
See application file for complete search history.

(56) References Cited

U.S. PATENT DOCUMENTS

| | | | |
|---|---|---|---|
| 11,419,846 B2 * | 8/2022 | Muscarella | A61P 43/00 |
| 2016/0015818 A1 * | 1/2016 | Taha | A61K 31/60 514/159 |
| 2018/0344676 A1 | 12/2018 | Hoag | |
| 2021/0046040 A1 | 2/2021 | Avram | |
| 2021/0346276 A1 | 11/2021 | Mitchell | |
| 2021/0346310 A1 * | 11/2021 | Plakogiannis | A61K 47/10 |
| 2022/0062221 A1 | 3/2022 | Hanlon | |

FOREIGN PATENT DOCUMENTS

| | | | |
|---|---|---|---|
| WO | 2020/220092 A1 | 11/2020 | |
| WO | WO-2021236782 A1 * | 11/2021 | |

* cited by examiner

*Primary Examiner* — Raymond J Henley, III (74) *Attorney, Agent, or Firm* — Caldwell Intellectual Property Law, LLC (57) ABSTRACT

A cannabinoid formulation includes a cannabinoid composition, an anti-inflammatory ingredient, an additive, and a delivery vehicle. The cannabinoid composition is in the amount of 0.1% to 15% of the final concentration of the formulation. The anti-inflammatory ingredient is in the amount of 10% to 30% of the final concentration of the formulation. The additive is in the amount of 1% to 5% of the final concentration of the formulation. The cannabinoid formulation is designed to be administrated topically to a target area on a human.

8 Claims, 5 Drawing Sheets

| Cannabinoid Composition | Anti-Inflammatory Ingredient | Terpene | Stabilizer | Additive | | Numbing Agent | Vitamin | Additional Agents |
|---|---|---|---|---|---|---|---|---|
| | | | | Emulsifier | Homeopathic Ingredient | | | |
| cannabis | acetaminophen | | | | | | | |
| hemp | NSAIDS | menthol | tris(2,4-di-tert-butylphenyl)phosphite | amphiphilic surfactants | lavender | Lidocaine | magnesium | moisturizing element |
| tetrahydrocannabinol | aspirin | eucalyptol | Salpn | lecithin | peppermint | Benzocaine | calcium | ionic liquids |
| tetrahydrocannabivarin | naproxen | limonene | benzophenone | soy lecithin | artica | Pramoxine | vitamin D | delivery vehicle |
| cannabichromene | ibuprofen | terpenoids | benzotriazole | mucilage | crab apple | Dibucaine | omega-3 fatty acids | |
| cannabichromanon | diclofenac | eicosenoic acid | polysorbate 60 | sodium phosphate | rock rose | Proparacaine | niacin | |
| cannabidiol | ketoprofen | erucic acid | stearyl alcohol | monoglyceride | clematis | Betacaine | vitamin B-12 | |
| cannabielson | natural products | oleic acid | cetyl alcohol | diglyceride | impatiens | Tetracaine | vitamin B-2 | |
| cannabidivarin | | palmitic acid | citric acid | sodium stearoyl lactylate | cherry plum | | vitamin E | |
| cannabifuran | | monoterpenoids | dehydrated alcohol | diacetyl tartaric acid ester monoglyceride | star of Bethlehem | | | |
| cannabigerol | | peppermint oikt | lactic acid | diacetyl tartaric acid ester monoglyceride | borage oil | | | |
| cannabicyclol | | | glycol | cellulose | turmeric | | | |
| cannabinol | | | glycerin | sodium caseinate | cat's claw | | | |
| cannabinodiol | | | oxygen scavengers | polysorbate 20 | eucalyptus | | | |
| cannabitriol | | | antiozonants | ceteareth 20 | frankincense | | | |
| cannabivarin | | | sequestrants | detergents | aloe vera | | | |
| isocannabinoids | | | ultraviolet stabilizers | | cinnamon | | | |
| Delta-8 THC | | | | | thunder god vine | | | |
| Delta-9 THC | | | | | ginger | | | |
| | | | | | methylsulfonylmethane | | | |
| | | | | | glucosamine | | | |
| | | | | | achoitin | | | |
| | | | | | creatine | | | |
| | | | | | fish oil | | | |

CANNABIDIOL FORMULATION FOR ALLEVIATING PAIN AND A METHOD OF MANUFACTURING

FIELD OF THE INVENTION

The present invention generally relates to the field of plant chemistry and pharmacology. In particular, the present invention is directed to a cannabidiol formulation for alleviating pain and a method of manufacturing.

BACKGROUND

Chemical extracts derived from plants have beneficial effects on both humans and animals. For example, cannabidiol oil which comes from cannabis and hemp sources has beneficial effects easing symptoms of many common health issues, including arthritis, muscle aches, and stiffness. It can be difficult to harness a multitude of health benefits in a single formulation while, resulting in a user to take undesired chemicals or substances into his or her body.

SUMMARY OF THE DISCLOSURE

In an aspect a cannabinoid formulation for alleviating pain includes: a cannabinoid composition in the amount of 0.1% to 15% of the final concentration of the cannabinoid formulation; an anti-inflammatory ingredient in the amount of 10% to 30% of the final concentration of the cannabinoid formulation; an additive in the amount of 1% to 5% of the final concentration of the cannabinoid formulation; and a delivery vehicle configured to enhance the absorption of the cannabinoid formulation and configured to deliver the cannabinoid formulation topically.

In another aspect a method of manufacturing a cannabinoid formulation for alleviating pain includes receiving a cannabinoid composition in the amount of 0.1% to 15% of the final concentration of a cannabinoid formulation, receiving an anti-inflammatory ingredient in the amount of 10% to 30% of the final concentration of the cannabinoid formulation, receiving an additive in the amount of 1% to 5% of the final concentration of the cannabinoid formulation, combining the cannabinoid composition, the anti-inflammatory ingredient, and the additive to create a formulation, and designing a delivery vehicle to be applied to a user, wherein the delivery carrier is further configured to enhance the absorption of the cannabinoid formulation and deliver the cannabinoid formulation topically.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a block diagram illustrating an exemplary embodiment of ingredients contained within the formulation;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a cannabinoid formulation for alleviating pain and method of manufacturing. Aspects of the present disclosure can be used topically on an area of pain to alleviate pain. Alleviating pain may include targeting inflammation. Aspects of the present disclosure may be suspended and/or mixed in a cream to be administered to a user. Exemplary embodiments illustrating aspects of the present disclosure are described below in the context of several specific examples.

Figure 1:
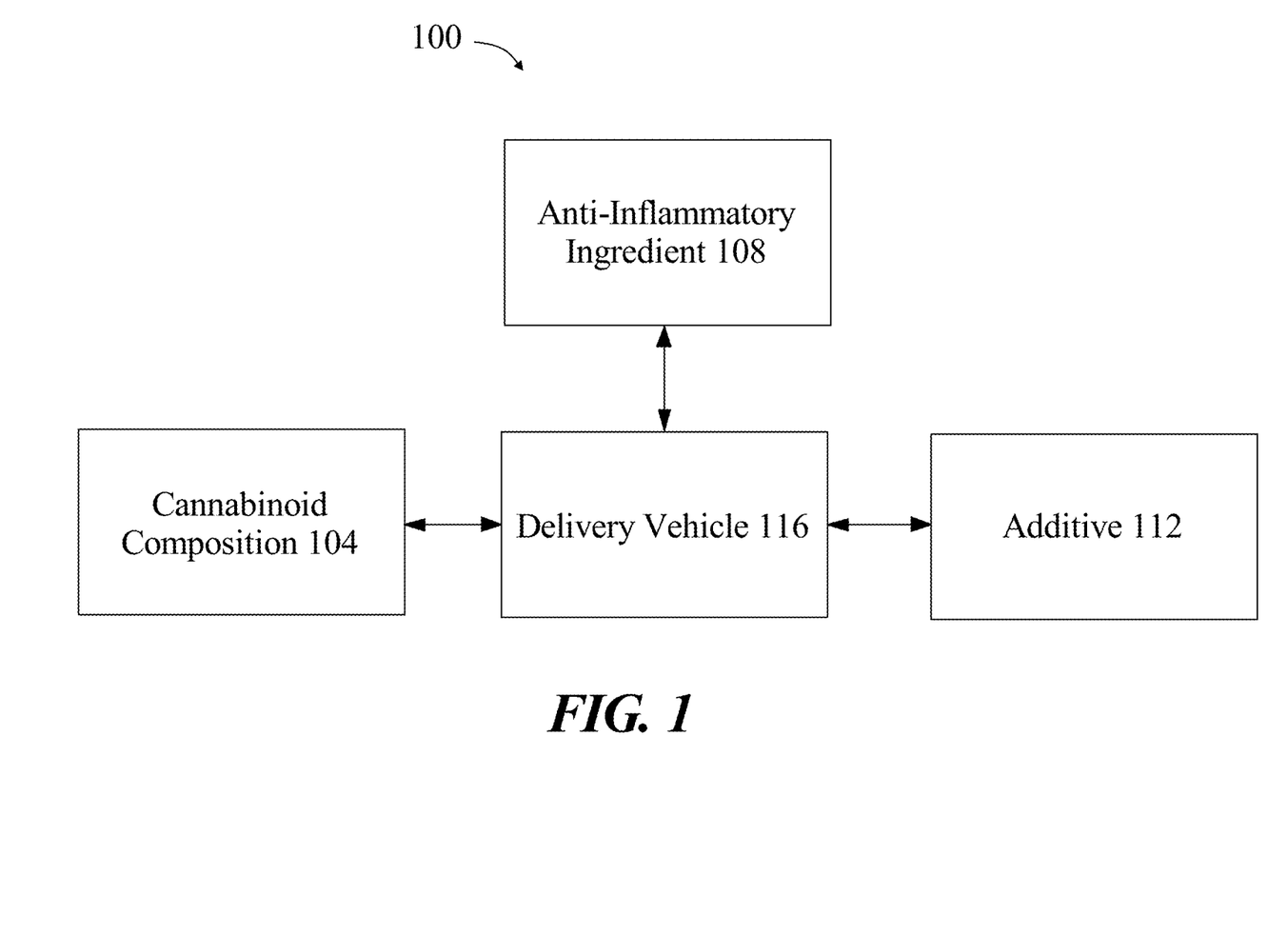
FIG. 1 is a block diagram illustrating an exemplary embodiment of a cannabinoid formulation for alleviating pain.

Referring now to the drawings, FIG. 1 illustrates a block diagram of a cannabinoid formulation 100 for alleviating pain. Cannabidiol formulation may include a cannabinoid composition 104. As used herein, a "cannabinoid composition" is a combination of one or more various chemicals found in or derived from a cannabis plant. A cannabis plant may include any genus of flowering plants within the family Cannabaceae. The cannabinoid composition 104 may be sourced from one or more plants including but not limited to Cannabis Sativa (strains may include but are not limited to Acapulco Gold, Panama Red, and/or Durban Poison), Cannabis Indica (strains may include but are not limited to Hindu Kush, Afghan Kush, and/or Granddaddy Purple), and/or a hybrid plant (strains may include but are not limited to Pineapple Express, Trainwreck, and Blue Dream). A cannabis plant may include a hybrid plant. As used herein, a "hybrid plant" is a plant created from the cross-pollination of two different varieties of a plant. A cannabinoid composition 104 may include cannabinoid elements. Cannabinoid elements may include, as non-limiting examples, cannabis, hemp, tetrahydrocannabinol (THC), tetrahydrocannabinol (THCA), tetrahydrocannabivarin (THCV), cannabichromene (CBC), cannabichromanon (CBCN), cannabidiol (CBD), cannabielsoin (CBE), cannabidivarin (CBDV), cannbifuran (CBF), cannabigerol (CBG), cannabicyclol (CBL), cannabinol (CBN), cannabinodiol (CBDN), cannabitriol (CBT), cannabivarin (CBV), isocanabinoids, and/or other compounds that act on a cannabinoid receptor. THC may include, as non-limiting examples, Delta-8 THC, Delta-9 THC, and/or other types of THC. Cannabinoid elements may be presented as a cannabidiol oil. In an embodiment, cannabinoid composition may be presented in the amount of 0.1% to 15% of the final concentration of the formulation 100. In an embodiment, cannabinoid elements may be presented at a concentration up to 5000 milligrams per milliliter. Cannabidiol oils may be free of glyphosate. Cannabidiol oils may be pesticide free, formaldehyde free, and contain a low carcinogen risk due to the absence of formaldehyde. Cannabidiol oils may be sourced from plant species that include for example, Cannabis Sativa and Cannabis Indica. Cannabidiol oils including both cannabis oil and hemp oil sourced from plant species may be suspended and/or dissolved in a lipophilic oil that may include for example avocado oil, canola oil, coconut oil, corn oil, cottonseed oil, flaxseed oil, grape seed oil, olive oil, palm oil, palm kernel oil, peanut oil, safflower oil, soybean oil, linoleic oil, oleic oil, walnut oil, sesame oil, medium chain triglyceride oil (MCT), cottonseed oil, palm oil, Vitamin E oil, cocoa butter, fish oil, single cell oils, rapeseed oil, safflower oil, almond oil, beech nut oil, brazil nut oil, cashew oil, hazelnut oil, macadamia oil, mongongo nut oil, pecan oil, pine nut oil, pistachio oil, pumpkin seed oil, grapefruit seed oil, lemon oil, orange oil, bitter gourd oil, buffalo gourd oil, butternut squash seed oil, egusi oil, watermelon seed oil, acai oil, black seed oil, blackcurrant seed oil, borage seed oil, evening primrose oil, amaranth oil, apricot oil, apple seed oil, argan oil, babassu oil, ben oil, borneo tallow nut oil, cape chestnut oil, carob pod oil, cocoa butter oil, cocklebur oil, cohune oil, cordiander seed oil, date seed oil, dika oil, false flax oil, hemp oil, kapok seed oil, kenaf seed oil, lallemantia oil, manila oil, meadowfoam seed oil, mustard oil, niger seed oil, nutmeg butter oil, okra seed oil, papaya seed oil, perilla seed oil, persimmon seed oil, pequi oil, pili nut oil, pomegranate seed oil, poppyseed oil, pracaxi oil, prune kernel oil, quinoa oil, ramtil oil, rice bran oil, royle oil, sacha inchi oil, sapote oil, seje oil, shea butter oil, taramira oil, tea seed oil, thistle oil, tigernut oil, tomato seed oil, wheat germ oil, and any combination thereof.

Still referencing FIG. 1, cannabinoid composition 104 may include a ratio between two or more cannabinoid elements. In an embodiment, cannabinoid composition 104 may include a ratio of THC to CBD, CBD to CBG, THC to CHG, and the like. The ratio of one or more cannabinoid elements may include a ratio of the 0.1-15% cannabidiol component of the entire composition. For example, a ratio of 20% THC and 80% CBD would be that ratio of the entire 0.1-15% cannabidiol component of the entire composition. For example, cannabidiol composition 104 may include 20% THC and 80% CBD, 0.1% THC and 99.9% CBD, 5% THC and 95% CBD, or the like. Alternatively, cannabidiol composition 104 may include 20% CHG and 80% CBD, 0.1% CHG and 99.9% CBD, 5% CHG and 95% CBD, and the like. Alternatively, cannabidiol composition 104 may include 20% THC and 80% CHG, 0.1% THC and 99.9% CHG, 5% THC and 95% CHG, and the like. Alternatively, cannabidiol composition 104 may include a combination of THC, CBD, and CBG. In an embodiment, cannabidiol composition 104 may include 0.1% THC, 0.1% CHG, and 99.8% CBD. In another embodiment, cannabidiol composition 104 may include 5% THC, 5% CHG, and 90% CBD.

With continued reference to FIG. 1, cannabinoid composition 104 may contain beneficial health effects, such as analgesic, anti-inflammatory, antineoplastic and chemo preventive effects. Cannabinoid composition 104 may exert its anti-proliferative, anti-angiogenic and pro-apoptotic activity through various mechanisms such as by stimulating endoplasmic reticulum (ER) stress and inhibits AKT/mTOR signaling, thereby activating autophagy and promoting apoptosis. Additionally, cannabinoid composition 104 (also referred to as "composition 104") may enhance the generation of reactive oxygen species (ROS), which further enhances apoptosis. ROS may upregulate the expression of intercellular adhesion molecule 1 (ICAM-1) and tissue inhibitor of matrix metalloproteinases-1 (TIMP1) and may decrease the expression of inhibitor of DNA binding 1 (ID-1). This may inhibit cancer cell invasiveness and metastasis. Composition 104 may also activate the transient receptor potential vanilloid type 2 (TRPV2), which may increase the uptake of various cytotoxic agents in cancer cells. The analgesic effect of composition 104 may be mediated through the binding of this agent to and activation of CB1. The induction of apoptosis by composition 104 may allow for anti-inflammatory effects.

Continuing to reference FIG. 1, formulation 100 includes an anti-inflammatory ingredient 108. An anti-inflammatory ingredient 108 may include acetaminophen, nonsteroidal anti-inflammatory drugs (NSAIDS), aspirin, naproxen, ibuprofen, diclofenac, ketoprofen, and the like. Anti-inflammatory ingredient 108 may be presented as a cream, gel, or any other topical forms. Anti-inflammatory ingredient 108 may be used present in conjunction with composition 104 to treat symptoms of arthritis, and the like. They may relieve pain and swelling. As used herein, "pain" is an unpleasant sensory and emotional experience associated with, or resembling that associated with, damage of the human body. Pain may be associated with medical conditions such as, but not limited to, arthritis, joint pain, neck pain, cancer pain, headaches, muscle pan, Fibromyalgia, Lyme disease, Multiple sclerosis, Rheumatoid arthritis, back pain, bruising, sports injuries, Tendonitis, Bursitis, strains, sprains, knee injuries, rotator cuff injuries, fractures, dislocations, shoulder injuries, tennis or golf elbow, hamstring strain, Sciatica, shin splits, groin pull, concussion, ACL tear, Patellofemoral syndrome, plantar fasciitis, ankle sprains, and the like. Anti-inflammatory ingredient 108 may work by blocking enzymes, such as cyclooxygenase (COX) enzymes. The inhibition of COX-1 and COX-2 may provide pain-relieving and anti-inflammatory effects. Anti-inflammatory ingredient 108 may be present at a concentration of between 10-30% of the final concentration of the formulation 100. Alternatively, anti-inflammatory ingredient 108 may be present at a concentration of 30-50% of the final concentration of the formulation 100. Specifically, ibuprofen may be present at a concentration of 10-20%, diclofenac at 10-15%, ketoprofen at 10-20%, aspirin at up to 10%, acetaminophen at up to 10%, and naproxen at 10-15%. In some embodiments, anti-inflammatory ingredient 108 may include a combination of two or more anti-inflammatory ingredients. For example, anti-inflammatory ingredient 108 may include 10% ibuprofen and 10% ketoprofen or it may include 10% ketoprofen and 5% diclofenac.

Continuing to reference FIG. 1, and in an embodiment, anti-inflammatory ingredient 108 may be a natural product. Natural product may include, without limitation, Capsaicin, Evening primrose oil, magnesium, ginger, CatsClaw, Boswellia, White willow bark, essential oils, and Corydalis yanhunsuo. Natural product may be present at a concentration of between 10-30% of the final concentration of formulation 100. In some embodiments, anti-inflammatory ingredient 108 may include a combination of two or more natural products. For example, anti-inflammatory ingredient 108 may include 10% CatsClaw and 5% white willow bark, or the like.

Still referencing FIG. 1, formulation 100 may include an additive 112. As used in this disclosure an "additive" is a substance and/or product that improves and/or preserves the effect of formulation 100. Additive 112 may be present in the amount of 1-5% of the final concentration of formulation 100. Alternatively, additive 112 may be present in the amounts of 5-20% of the final concentration of formulation 100. In an embodiment, and without limitation, additive 112 may include a terpene. As used in this disclosure a "terpene" is an unsaturated hydrocarbon consisting of the chemical composition $(C_5H_8)_n$. For example, and without limitation, terpene may comprise one or more monoterpenes, sesquiterpenes, diterpenes, and the like thereof. As a further non-limiting example, terpene may include, without limitation, menthol, eucalyptol, limonene, terpenoids, eicosanoid acid, eruic acid, oleic acid, palmitic acid, monoterpenoids, bisabol, caryophyllene, linalool, myrcene, ocimene, pinene, terpinolene, humulene, eucalyptol, peppermint oil, etc. In an embodiment, and without limitation, terpene may increase a disease resistance. In another embodiment, and without limitation, terpene may increase cell growth. In another embodiment, and without limitation, terpene may produce an aromatherapeutic effect. In another embodiment, and without limitation terpene may enhance an absorption of one or more components of formulation 100. In an embodiment and without limitation, absorption may be calculated as a function of a partition coefficient, wherein a "partition coefficient," as used herein, is the ratio of concentration of substances and/or analytes in composition 100 and concentration of substances and/or analytes in cells and/or tissues. For example, and without limitation partition coefficient may be calculated by:

$$\frac{[x]_1}{[x]_2} = K_{N(x,12)}$$

wherein, $K_{N(x,12)}$ is the partition coefficient, $[x]_1$, is the concentration of a first analyte and/or substance, and $[x]_2$, is the concentration of a second analyte and/or substance. In an embodiment, and without limitation, partition coefficient may be modified and/or varied as a function of temperature. For example, and without limitation, as temperature increases partition coefficient may increase. As a further non-limiting example, as temperature decreases partition coefficient may decrease. In an embodiment, and without limitation, concentration of the first analyte and/or substance and/or second analyte and/or substance may be calculated as a function of an ideal gas law, wherein an "ideal gas law," is an equation to calculate the state of a gas and is calculated by:

$$PV=nRT$$

wherein, P is the pressure, V is the volume, n is the amount of a substance and/or analyte, R is the ideal gas constant, and T is the temperature. Terpenes may include but are not limited to myrcene, beta-myrcene, alpha bisabolol (bisobol), alpha phellandrene, alpha pinene, beta caryophyllene, beta pinene, borneol, cadinene, camphene, camphor, carene, 1,8-cineole, citral, citronellol, delta 3 carene, eucalyptol, eugenol, gamma terpinene, geraniol, humulene, limonene, linalool, nerol, nerolidol, trans-nerolido, ocimene, para-cymene, phytol, pulegone, sabinene, terpineol, terpinolene, valencine and/or any combination of the above.

Still referencing FIG. 1, additive 112 may include a stabilizer. As used in this disclosure a "stabilizer" is a substance and/or analyte that prevents degradation of formulation 100. For example, and without limitation, stabilizer may include tris(2,4-di-tert-butylphenyl) phosphite. As a further non-limiting example, stabilizer may include Salpn. As a further non-limiting example, stabilizer may include benzophenone and/or benzotriazole. As a further non-limiting example, stabilizer may include polysorbate 60. As a further non-limiting example, stabilizer may include stearyl alcohol, cetyl alcohol, citric acid, dehydrated alcohol, lactic acid, and the like thereof. As a further non-limiting example, stabilizer may include glycol. As a further non-limiting example, stabilizer may include glycerin. As a further non-limiting example, stabilizer may include oxygen scavengers. As a further non-limiting example, stabilizer may include radical scavengers. As a further non-limiting example, stabilizer may include antiozonants. As a further non-limiting example, stabilizer may include sequestrants. As a further non-limiting example, stabilizer may include ultraviolet stabilizers. In an embodiment, and without limitation, additive 112 may comprise an emulsifier. As used in this disclosure an "emulsifier" is a substance and/or analyte that stabilizes an emulsion. An "emulsion", as used herein, is a mixture of two or more liquids that are normally immiscible. In an embodiment, and without limitation, emulsifier may stabilize an emulsion as a function of increasing a kinetic stability. In another embodiment, and without limitation, emulsifier comprise one or more amphiphilic surfactants. As used in this disclosure an "amphiphilic surfactant" is a compound that has a polar hydrophilic portion and a non-polar hydrophobic portion. In an embodiment, and without limitation, amphiphilic surfactants may produce one or more oil-in-water emulsions and/or water-in-oil emulsions. In an embodiment, and without limitation, emulsifier may comprise lecithin, soy lecithin, mucilage, sodium phosphate, monoglyceride, diglyceride, sodium stearoyl lactylate, diacetyl tartaric acid ester monoglyceride, diacetyl tartaric acid ester diglyceride, cellulose, sodium caseinate, and the like thereof. In another embodiment, and without limitation, emulsifier may comprise polysorbate 20, ceteareth 20, detergents, and the like thereof.

Continuing to reference FIG. 1, additive 122 may include a homeopathic ingredient. As used herein, a "homeopathic ingredient" is a substance that is derived from plants, minerals, and animal substances. In an embodiment, and without limitation, additive 122 may include homeopathic ingredients such as lavender, peppermint, arnica, crab apple, rock rose, clematis, impatiens, cherry plum, star of Bethlehem, and the like. Additionally, homeopathic ingredients may also include herbs such as, without limitation, borage oil, turmeric, cat's claw (Uncaria tomentosa), eucalyptus, frankincense, aloe vera, cinnamon, thunder god vine, ginger, and the like. Additionally, homeopathic ingredients may include methylsulfonylmethane (MSM), glucosamine, adroitin, creatine, fish oil and the like. Homeopathic ingredient/ingredients may be used in formulation 100 for their pain relieving properties. Homeopathic ingredients may be used in concurrence with non-homeopathic pain relieving elements such as those discussed as an anti-inflammatory ingredient 108. For example, there may be a ratio of MSM to acetaminophen, a ratio of diclofenac to turmeric, a ratio of borage oil to ketoprofen, and the like.

Still referencing FIG. 1, additive 112 may include a numbing agent. As used herein, "numbing agent" is a local anesthesia used to deprive a person of the power of sensation at a given location. In an embodiment, and without limitation, additive 112 may include numbing agents such as lidocaine, benzocaine, pramoxine, dibucaine, proparacaine, betacaine, tetracaine. Numbing agents, in an embodiment, may be present at a concentration of between 1-10% of the final concentration of formulation 100. Numbing agents may be used for their pain reliving properties. Numbing agents may be used in conjunction with any additive 112 as discussed herein.

Still referencing FIG. 1, additive 122 may include a vitamin. As used herein, a "vitamin" is an organic compound that is essential for normal human growth and nutrition. In an embodiment, and without limitation, vitamins may include magnesium, calcium, vitamin D, omega-3 fatty acids, niacin, vitamin B-12, vitamin B-2, and the like. Vitamins may be present in small quantities in additive 112.

For example, vitamin may be present at a concentration of 0.01-1% of additive 112. Additive 112 may also include vitamin E. Vitamin E may be used as an antioxidant to prevent the oxidation of oils, such as oils found in composition 104. Additionally, vitamin E may be used to prevent deterioration in natural products such as homeopathic ingredients. Vitamin E may be used to prolong the shelf life of formulation 100. Other vitamins, such as magnesium, vitamin B-12, vitamin B-2, and the like may be used to treat inflammation. Vitamins may include natural anti-inflammatory properties that when used in conjunction with the other ingredients in formulation 100, may decrease inflammation in a user.

Still referencing FIG. 1, formulation 100 may include a delivery vehicle 116. As used herein, a "delivery vehicle" is a component that allows formulation 100 to be applied. Delivery vehicle 116 may be configured to enhance stability of composition 104, anti-inflammatory ingredient 108, additive 112, the combination thereof, and the like. In some embodiments, delivery vehicle 116 may increase a delivery of formulation 100 to the skin or the like. A stability of delivery vehicle 116 may improve a patient adherence to using formulation 100. As used in this disclosure a "stability" is a measurable value denoting the magnitude of reactivity of a compound. For example, and without limitation, stability may denote that composition 104 has a high stability as a function of a low Gibbs Free Energy. As a further non-limiting example, stability may denote that additive 116 has a low stability as a function of a high Gibbs Free Energy. In an embodiment, and still referring to FIG. 1, delivery vehicle 116 may dissolve and/or liquefy composition 104, anti-inflammatory ingredient 108, and/or additive 112 as a function of a solubility property, wherein solubility properties are described below. In another embodiment, and without limitation, delivery vehicle 116 may suspend and/or mix composition 104, anti-inflammatory ingredient 108, and/or additive 112 as a function of an emulsion. In an embodiment, and without limitation, delivery vehicle 116 may suspend and/or mix composition 104, anti-inflammatory ingredient 108, and/or additive 112 as a function of a liposome, nanoliposome, nano-lipid sphere, transfersome, noisome, ethosome, nanovesicle, and the like thereof. Additionally, and in an embodiment, delivery vehicle 116 may apply the vasodilator 104 uniformly to the skin of a human. Uniform application may allow for uniform distribute of formulation 100. Application of the composition is discussed in further detail below.

Still referring to FIG. 1, ionic liquid may comprise a room-temperature ionic liquid. As used in this disclosure a "room-temperature ionic liquid" is an ionic liquid that exists in a liquid state at room temperature. For example, and without limitation, room-temperature ionic liquid may comprise one or more salts derived from 1-methylimidazole. For example, and without limitation, salts derived from 1-methylimidazole may include 1-alkyl-3-methylimidazolium, 1-ethyl-3-methyl, 1-butyl-3-methyl, 1-octyl-3-methyl, 1-decyl-3-methyl, 1-dodecyl-3-methyl-dodecyl, and the like thereof. As a further non-limiting example, salts derived from 1-methylimidazole may include 1-butyl-2,3-dimethylimidazolium, 1,3-di(N,N-dimethylaminoethyl)-2-methylimidazolium, 1-butyl-2,3-dimethylimidazolium, and the like thereof. In an embodiment, and without limitation, room-temperature ionic liquid may comprise one or more cations derived from pyridine such as, but not limited to 4-methyl-N-butyl-pyridinium, N-octylpyridinium, and the like thereof. In another embodiment, and without limitation, room-temperature ionic liquid may comprise one or more cations such as tetraethylammonium, tetrabutyl ammonium, phosphonium, and the like thereof cations. Additionally or alternatively, room-temperature ionic liquid may comprise one or more anions such as but not limited to tetrafluoroborate, hexafluorophosphate, bis-trifluoromethanesulfonimide, trifluoromethanesulfonate, dicyanamide, hydrogen sulphate, ethyl sulphate, and the like thereof. In an embodiment, and without limitation, ionic liquid may be comprised of a low-temperature ionic liquid, protic ionic liquid, poly-ionic liquid, magnetic ionic liquid, and the like thereof. In another embodiment, ionic liquids may increase transcellular transport as a function of a choline-based bioinspired ionic liquid, such as but not limited to, choline phenylalaninate. In another embodiment, ionic liquids may increase permeation rate as a function of an imidazole based ionic liquid such as, but not limited to, ionic liquids derived from 1-methylimidazole as described above.

Still referring to FIG. 1, delivery vehicle 116 may include a cream. As used herein, a "cream" is a thick liquid or semisolid cosmetic or medical preparation applied to the skin. A cream may include Rescue cream, Arnica cream, and the like. Delivery vehicle 116 may also include Emu oil, Arnica gel, and the like. Composition 104, anti-inflammatory ingredient 108, and/or additive 112 may be combined/mixed in with the aforementioned creams to make a cream of formulation 100. Cream may also include anti-inflammatory effects and may contribute to the pain alleviating properties of formulation 100. A cream may be applied to a human's/user's skin by way of an applicator. An "applicator" as used herein, is a device used for applying a substance to a surface. An applicator may include a spoon, a stick, a rollerball, a sponge, a finger, or the like. A cream may include a moisturizing element such as, but not limited to, such as, but not limited to, petrolatum, hydrocarbons, petroleum jellies, soft paraffins, multi-hydrocarbons, jojoba oil, coconut oil, palmitic acid, palmitoleic acid, stearic acid, oleic acid, arachidic acid, 11-eicosenoic acid, lignoceric acid, caprylic acid, capric acid, lauric acid, myristic acid, and the like thereof. In other embodiments, delivery vehicle 116 may also be a gel, ointment, scrub, wash, lotion, a combination thereof, and the like for topical administration. For example, a cream may be a lotion. A scrub may also be a lotion if it includes moisturizing properties. An ointment may also be a cream. In an embodiment, formulation 100 may be applied topically to various parts on the body such as when formulated as a cream or lotion. For example, a user with stiff knee joints from various conditions such as osteoarthritis or Lyme disease may apply formulation 100 to knee joint. In yet another non-limiting example, a user with a stiff neck from sleeping in an incorrect position or with jaw pain from temporomandibular joint (TMJ) may apply formulation 100 to back of neckline or along the jawline.

With continued reference to FIG. 1, the formulation 100 may further be provided to a user in varied manners. The formulation may be provided to a user in a capsule, tablet, lozenge, troche, suspension, suppository, orally disintegrating tablet, transdermal patch, an inhaled formulation and/or metered dose inhaler. Capsule may include, without limitation, hard-shelled capsules and soft-shelled capsules. Tablets may include, without limitation, solid unit dosage form of medications with suitable excipients and prepared either by molding and/or by compression. Transdermal patch may include, without limitation, an adhesive patch that is placed on the skin to deliver a specific dose of formulation through the skin and into the bloodstream, such as single-layer in-drug-adhesive, multi-layer drug-in-adhesive, reservoir, matrix, vapor patch, and the like. In an embodiment, cannabidiol formulation may be inhaled through a user's nostrils or mouth into the lungs for various non-federal drug administration approved effects that have yet to be completely elucidated through rigorous scientific research. In an embodiment, cannabidiol formulation inhalation may be facilitated through a vaporizer cartridge such as CLASSIC CATRIDGES and/or ELITE CARTRIDGES as produced by The Clear of California. In an embodiment, vaporizer cartridge may be utilized in conjunction with a battery device to heat cannabidiol formulation to a desired temperature to facilitate vaporization and subsequent inhalation by a user. Formulation 100 may be vaporized through the nose or mouth. Formulation 100 may be inhaled for 3-8 seconds through the mouth. Formulation 100 may be inhaled for 3-8 seconds through the nose. Persons skilled in the art, upon reviewing the entirety of this disclosure, will be aware of various manners to provide formulation to a user that may be applied in embodiments of the formulation as described above.

In an embodiment, and continuing to reference FIG. 1, topical administration of formulation 100 may be better than oral administration of formulation 100. In an embodiment, topical administration, such as through a cream or gel, may be localized and would prevent systemic absorption of formulation 100. In some embodiments, this may allow for the effects of formulation 100 to be targeted towards specific locations on the body. Additionally, topical administration of formulation 100 may bypass first pass hepatic metabolism. Because of this, a higher concentration of formulation 100 may reach the targeted location.

Still referencing FIG. 1, delivery vehicle 116 may use liposomes for liposomal delivery. As used herein, "liposomal delivery" is the delivery of substances into the body using liposomes. Liposomes, as used herein, are small artificial vesicles of spherical shape that can be created from cholesterol and natural non-toxic phospholipids. Liposomal delivery may include using liposomes for carrying formulation 100 to deeper layers of the user's epidermis. Liposomes may protect and stabilize ingredients in formulation 100 such as composition 104, anti-inflammatory ingredient 108, and/or additive 112. Formulation 100 may be found encapsulated in the aqueous space or intercalated into the lipid bilayer of a liposome.

Still referencing FIG. 1, liposomal delivery may be advantages to other vectors of topical and/or oral administration. Liposomal delivery may be noninvasive, which avoids pain and discomfort associated with injections and may decrease contamination risk. Additionally, liposomal delivery may have better bioavailability and delivery to cells, thus increasing absorption of formulation 100. Due to better bioavailability, formulation 100 may be effective in small doses. Additionally, liposomal delivery may protect various chemicals in formulation 100 from chemical and/or immunological breakdown and against the effect of enzymes in the body.

Still referencing FIG. 1, formulation 100 may alleviate pain as a function of a dosing frequency. As used in this disclosure a "dosing frequency" is a number of applications and/or doses that are provided to an individual at a specific concentration. For example, and without limitation, dosing frequency may denote that formulation 100 should be applied topically every 24 hours. In another embodiment, formulation 100 may be applied topically every 4-6 hours. In some embodiments, formulation 100 could be applied more frequently based on a pain condition it is being used for.

Now referring to FIG. 2, an exemplary embodiment of ingredients 200 contained within formulation 100 is illustrated. Formulation 100 may include a cannabinoid composition 104, wherein composition 104 includes any of the compositions 104 described above, in reference to FIG. 1, and wherein composition 104 may include but is not limited to any of the compositions contained within column 204. Formulation 100 may include an anti-inflammatory ingredient 108, wherein anti-inflammatory ingredient 108 includes any of the anti-inflammatory ingredient 108 described above, in reference to FIG. 1, and wherein anti-inflammatory ingredient 108 may include but is not limited to any of the anti-inflammatory ingredients 108 contained within column 208. Formulation 100 may include an additive 112, wherein additive 112 includes any of the additives 112 described above, in reference to FIG. 1, and wherein additive 112 may include but is not limited to any of the additive 112 contained within column 212. Additive 112 may further include a homeopathic ingredient, a vitamin, stabilizer, terpene, and the like. Formulation 100 may include an additional agent, wherein additional agents may include but are not limited to any of the additional agents contained within column 216. Additional agents may include but are not limited to room-temperature ionic liquid, moisturizing element, and the like.

Figure 3:
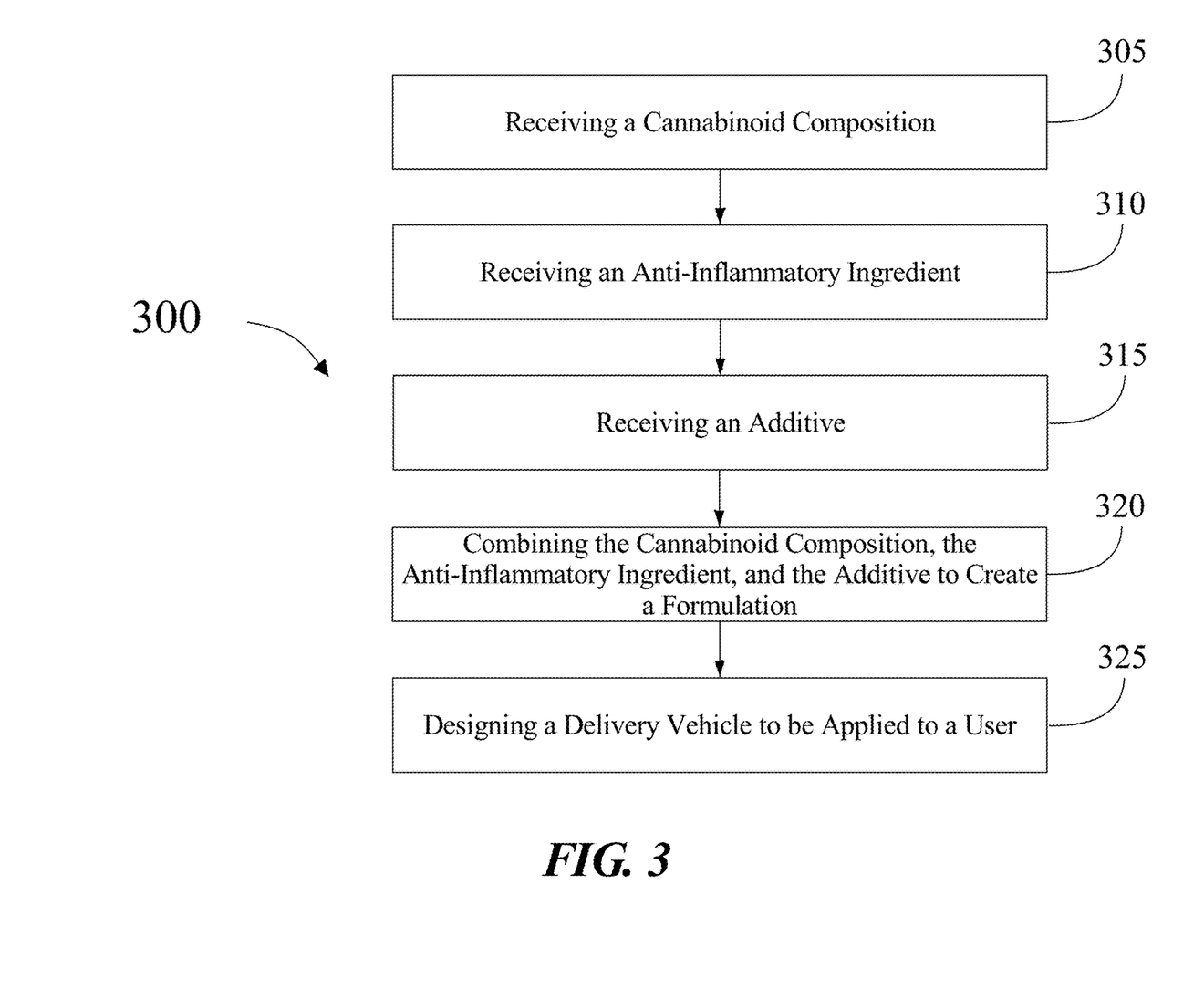
FIG. 3 is a block diagram illustrating an exemplary embodiment of a method of manufacturing a cannabinoid formulation for alleviating pain.

Now referring to FIG. 3, a method 300 of manufacturing a formulation for alleviating pain is shown. Step 305 of method 300 may include receiving a cannabinoid composition. The cannabinoid composition may include a ratio between two or more cannabinoid elements. Cannabinoid elements may include cannabinoid (CBD), tetrahydrocannabinol (THC), and cannabigerol (CBG), and the like. This step may be consistent with FIG. 1-2.

With continued reference to FIG. 3, step 310 of method 300 includes receiving an anti-inflammatory ingredient. The anti-inflammatory ingredient may include one or more of the following: acetaminophen, NSAIDS, naproxen, diclofenac, and aspirin. The anti-inflammatory ingredient may be in the amount of 10% to 30% of the final concentration of the cannabinoid formulation. This step may be consistent with FIG. 1-2.

With continued reference to FIG. 3, step 315 of method 300 includes receiving an additive. The additive may include a homeopathic ingredient. Additive may also include a vitamin, an emulsifier, and the like. This step may be consistent with FIG. 1-2.

With continued reference to FIG. 3, step 320 of method 300 includes combining the cannabinoid composition, the anti-inflammatory ingredient, and the additive to create a formulation. This step may be consistent with FIG. 1-2.

With continued reference to FIG. 3, step 325 of method 300 includes designing a delivery vehicle to be applied to a user, wherein the delivery carrier is further configured to enhance the absorption of the cannabinoid formulation and deliver the cannabinoid formulation topically. This step may be consistent with FIG. 1-2.

Figure 4:
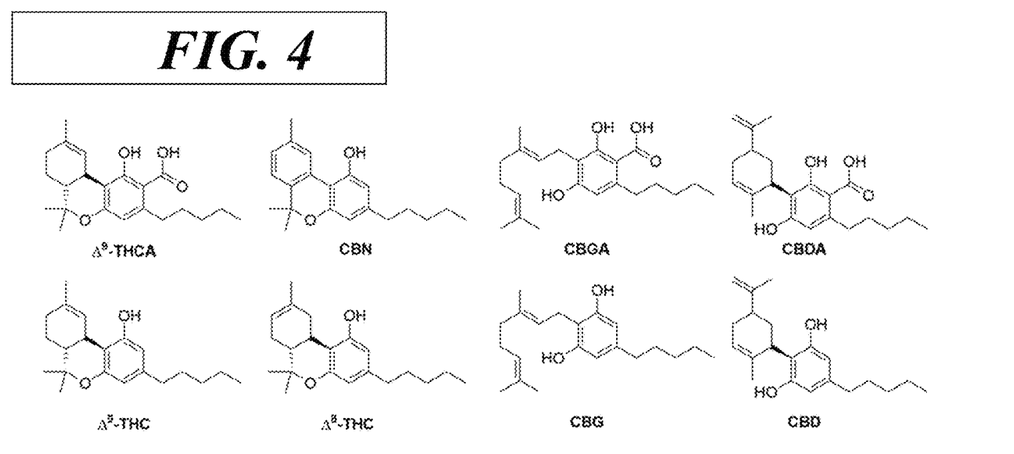
FIG. 4 is table of at least a chemical extract.

Referring now to FIG. 4, a table of at least a chemical extract is illustrated. At least a chemical extract may include a cannabinoid. A cannabinoid may include for example, a chemical extract such as CBDA, CBGA, CBD, CBG, CBN, Delta-8 THC, Delta-9 THC, and/or Delta-9 THCA as illustrated in FIG. 6.

Figure 5:
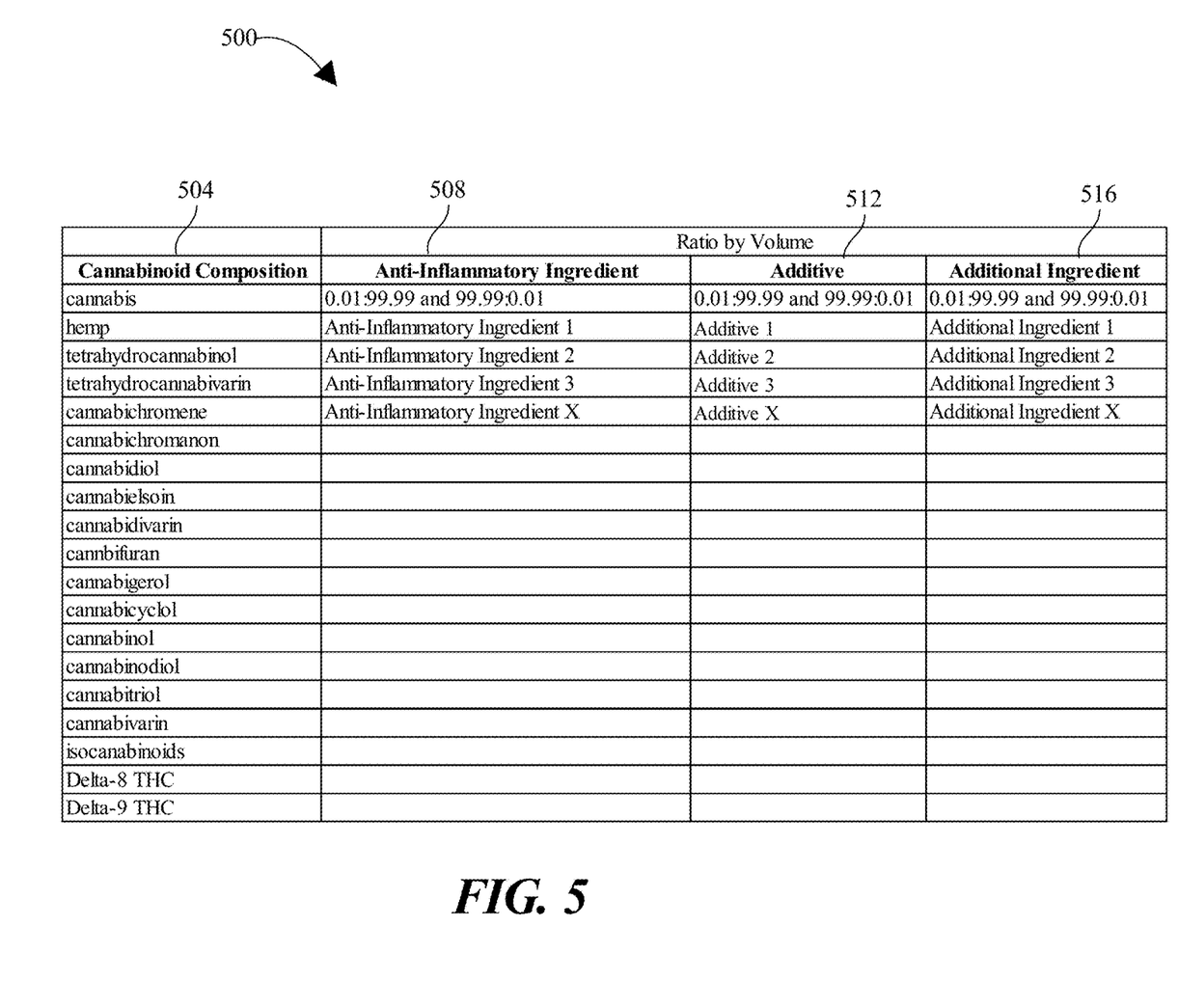
FIG. 5 is exemplary embodiment of ratio by volume of ingredients contained within formulation.

Referring now to FIG. 5, an exemplary embodiment 500 of ratio by volume of ingredients contained within formulation is illustrated. Formulation includes a cannabinoid composition. Cannabinoid composition may include any cannabinoids as discussed in FIG. 1 and as shown in column 504. Cannabinoid composition may be 0.1% to 15% of the final formulation. In an embodiment, cannabinoid composition may be composed of various quantities and concentrations of different cannabinoids. For instance and without limitation, cannabinoid composition may include 50% CBD, and 50% CBDA. In another embodiment, cannabinoid composition may include 20% THC and 80% CBG. In another embodiment, cannabinoid composition may include 80% CBD and 20% THC. Formulation may also include anti-inflammatory ingredients. Anti-inflammatory ingredients contained within column 508 may have a ratio by volume to the cannabinoid composition of between 0.01:99.99 and 99.99:0.01. Formulation may include a plurality of anti-inflammatory ingredients such as anti-inflammatory ingredient 1, anti-inflammatory ingredient 2, anti-inflammatory ingredient 3, and anti-inflammatory ingredient x, which may together in sum have a ratio by volume to the cannabinoid composition of between 0.01:99.99 and 99.99:0.01. For instance and without limitation, formulation may include anti-inflammatory ingredients such as ibuprofen, ketoprofen, diclofenac, aspirin, NSAIDS, and the like which together have a ratio by volume to the cannabinoid composition of between 0.01:99.99 and 99.99:0.01. Formulation includes additives. Additives contained within column 512 have a ratio by volume to the cannabinoid composition of between 0.01:99.99 and 99.99:0.01. Formulation may include a plurality of additives such as additive 1, additive 2, additive 3, and additive x, which may together in sum have a ratio by volume to the cannabinoid composition of between 0.01:99.99 and 99.99:0.01. For instance and without limitation, formulation may include additives such as terpenes, stabilizers, emulsifiers, homeopathic ingredients, numbing agents, and vitamins which together have a ratio by volume to the cannabinoid composition of between 0.01:99.99 and 99.99:0.01. Examples of additives such as terpenes, stabilizers, emulsifiers, homeopathic ingredients, numbing agents, and vitamins are discussed in further detail in FIG. 1. In yet another non-limiting example, formulation may include additives such at menthol, diglyceride, lavender, lidocaine, magnesium, and glycerin, and the like which may together in sum have a ratio by volume to the cannabinoid composition of between 0.01:99.99 and 99.99:0.01. Formulation may include additional ingredients. Additional ingredients contained within column 516 have a ratio by volume to the cannabinoid composition of between 0.01:99.99 and 99.99:0.01. Formulation may include a plurality of additional ingredients such as additional ingredient 1, additional ingredient 2, additional ingredient 3, and additional ingredient x, which may together in sum have a ratio by volume to the cannabinoid composition of between 0.01:99.99 and 99.99:0.01. For instance and without limitation, formulation may include additional ingredient such as moisturizing ingredients, ionic liquids, and the like which together have a ratio by volume to the cannabinoid composition of between 0.01:99.99 and 99.99:0.01. In yet another non-limiting example, formulation may include additional ingredient such jojoba oil, tetrafluoroborate, and the like which may together in sum have a ratio by volume to the cannabinoid composition of between 0.01:99.99 and 99.99:0.01.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A cannabinoid formulation for alleviating pain, the formulation comprising:
   a cannabinoid composition in the amount of 0.1% to 15% of the final concentration of the cannabinoid formulation;
   an anti-inflammatory ingredient in the amount of 10% to 30% of the final concentration of the cannabinoid formulation;
   an additive comprising a vitamin in the amount of 1% to 5% of the final concentration of the cannabinoid formulation; and
   a delivery vehicle configured to enhance the absorption of the cannabinoid formulation and configured to deliver the cannabinoid formulation topically.

2. The cannabinoid formulation of claim 1, wherein the cannabinoid composition comprises two or more cannabinoid elements.

3. The cannabinoid formulation of claim 2, wherein the two or more cannabinoid elements are selected from: tetrahydrocannabivarin (THCV), cannabichromene (CBC), cannabichromanon (CBCN), cannabidiol (CBD), cannabielsoin (CBE), cannabidivarin (CBDV), cannbifuran (CBF), cannabigerol (CBG), cannabicyclol (CBL), cannabinol (CBN), cannabinodiol (CBDN), cannabitriol (CBT), cannabivarin (CBV).

4. The cannabinoid formulation of claim 1, wherein one or more anti-inflammatory ingredient is selected from: acetaminophen, ibuprofen, naproxen, diclofenac, ketoprofen and aspirin.

5. The cannabinoid formulation of claim 1, wherein the additive comprises a homeopathic ingredient.

6. The cannabinoid formulation of claim 1, wherein the additive comprises an emulsifier.

7. A cannabinoid formulation for alleviating pain, the formulation comprising:
   a cannabinoid composition in the amount of 0.1% to 15% of the final concentration of the cannabinoid formulation;
   an anti-inflammatory ingredient in the amount of 10% to 30% of the final concentration of the cannabinoid formulation;
   an additive in the amount of 1% to 5% of the final concentration of the cannabinoid formulation; and
   a delivery vehicle comprising a cream, wherein the cream is selected from emu oil, rescue cream, and arnica cream, and is configured to enhance the absorption of the cannabinoid formulation and configured to deliver the cannabinoid formulation topically.

8. A cannabinoid formulation for alleviating pain, the formulation comprising:

a cannabinoid composition in the amount of 0.1% to 15% of the final concentration of the cannabinoid formulation;

an anti-inflammatory ingredient in the amount of 10% to 30% of the final concentration of the cannabinoid formulation;

an additive in the amount of 1% to 5% of the final concentration of the cannabinoid formulation; and a delivery vehicle comprises a liposomal delivery and is configured to enhance the absorption of the cannabinoid formulation and configured to deliver the cannabinoid formulation topically.

* * * * *